(12) United States Patent
Tzedakis et al.

(10) Patent No.: US 7,662,270 B2
(45) Date of Patent: Feb. 16, 2010

(54) ELECTROCHEMICAL REACTION METHOD AND MICROCHANNEL ELECTROCHEMICAL REACTOR AND ITS MANUFACTURING METHOD

(75) Inventors: Theodore Tzedakis, Toulouse (FR); Cheikhou Kane, Toulouse (FR); Anne Launay, Toulouse (FR)

(73) Assignees: Universite Paul Sabatier Toulouse III, Toulouse (FR); Centre National de la Recherche Scientifique (C.N.R.S.), Paris (FR)

( * ) Notice: Subject to any disclaimer, the term of this patent is extended or adjusted under 35 U.S.C. 154(b) by 637 days.

(21) Appl. No.: 11/281,434

(22) Filed: Nov. 18, 2005

(65) Prior Publication Data

US 2006/0108215 A1    May 25, 2006

Related U.S. Application Data

(60) Provisional application No. 60/631,877, filed on Dec. 1, 2004.

(30) Foreign Application Priority Data

Nov. 19, 2004    (FR) .................................. 04 12305

(51) Int. Cl.
C25B 1/00    (2006.01)
C25B 3/00    (2006.01)

(52) U.S. Cl. .................. 205/334; 205/413; 205/464
(58) Field of Classification Search .................. 205/334, 205/413, 464
See application file for complete search history.

(56) References Cited

U.S. PATENT DOCUMENTS

| | | | |
|---|---|---|---|
| 6,517,964 B2 * | 2/2003 | Mercuri | 429/30 |
| 6,541,145 B2 * | 4/2003 | Wilkinson et al. | 429/34 |
| 6,607,655 B1 | 8/2003 | Lowe et al. | 205/334 |
| 2003/0186107 A1 * | 10/2003 | Maston et al. | 429/38 |
| 2005/0019636 A1 * | 1/2005 | Kwon et al. | 429/32 |

FOREIGN PATENT DOCUMENTS

| | | |
|---|---|---|
| DE | 199 58 405 | 6/2001 |
| RU | 2320785 C1 * | 3/2008 |

* cited by examiner

*Primary Examiner*—Edna Wong
(74) *Attorney, Agent, or Firm*—Young & Thompson

(57) ABSTRACT

The invention relates to an electrochemical method and reactor in which at least one electrochemical reaction compartment (5, 6) comprises a plurality of microchannels whose grooves have a cross section of at least partially curved contour with a radius of curvature greater than 30 μm and an area of between 2500 μm² and 20000 μm². Application to the synthesis of diastereoisomers by continuous regeneration of NADH or NADPH.

22 Claims, 9 Drawing Sheets

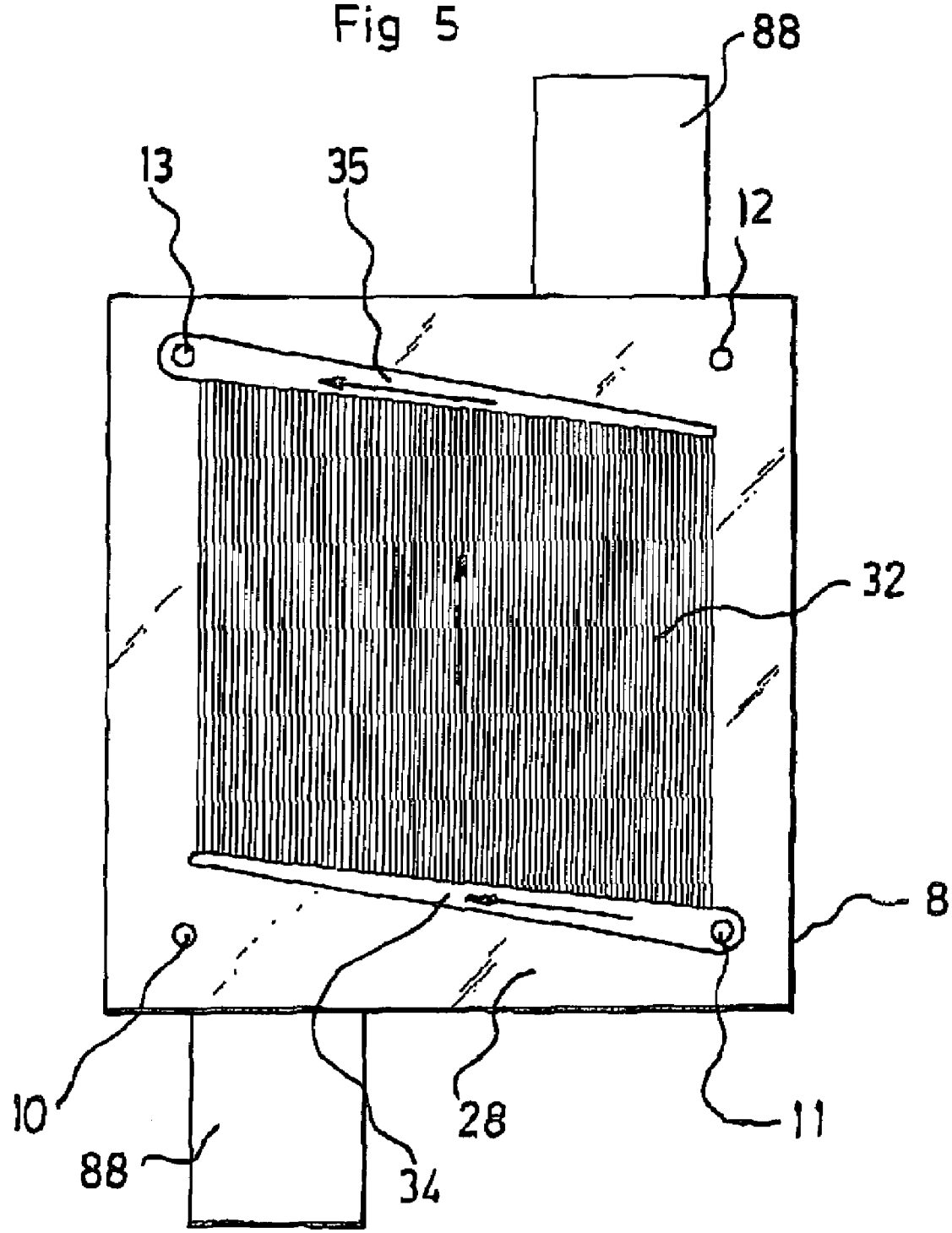

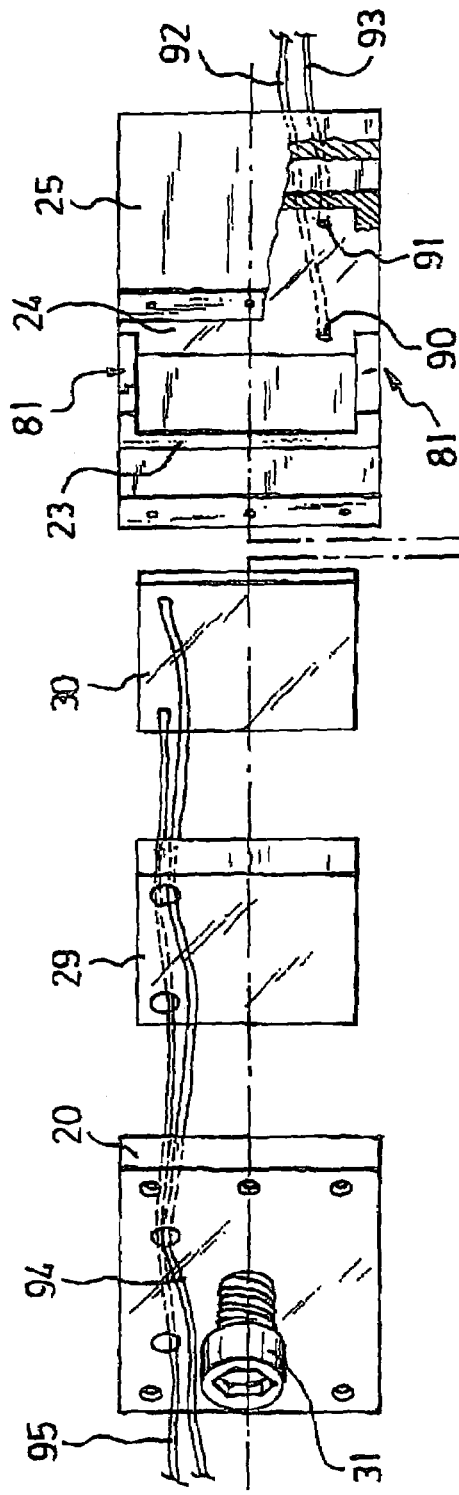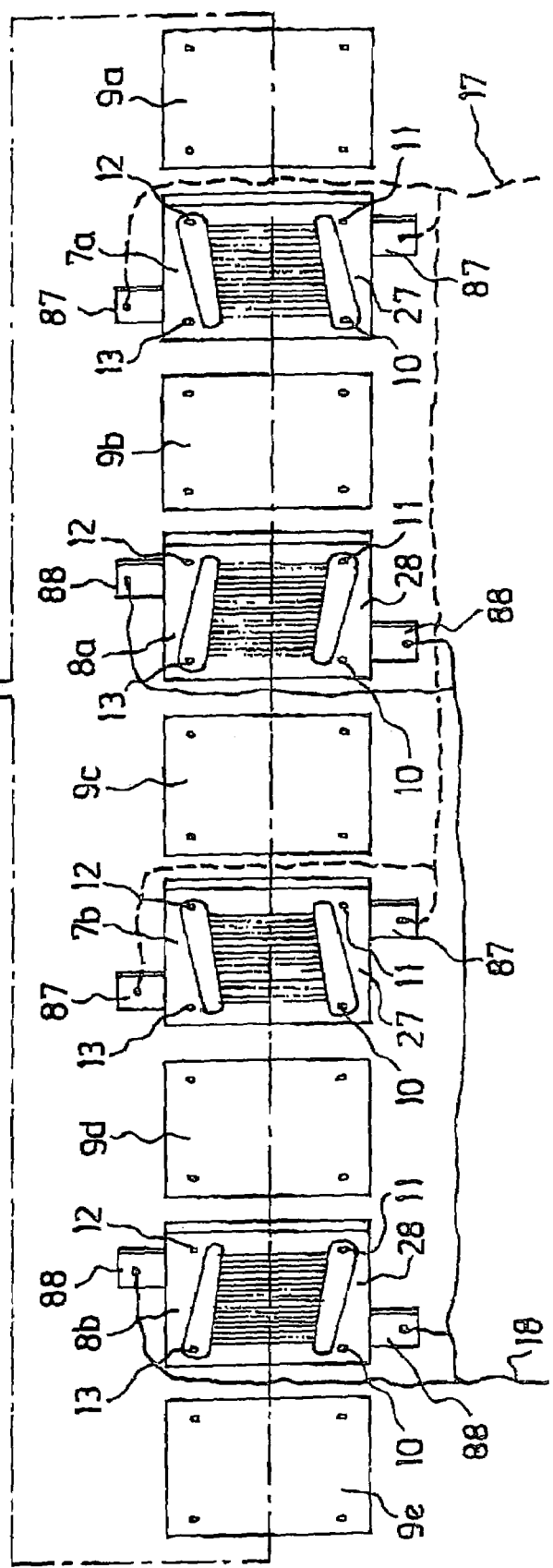
Fig 8

ELECTROCHEMICAL REACTION METHOD AND MICROCHANNEL ELECTROCHEMICAL REACTOR AND ITS MANUFACTURING METHOD

FIELD

The invention relates to an electrochemical method and reactor, as well as to a method for manufacturing such a reactor.

BACKGROUND

In certain applications, it is necessary to carry out electrochemical reactions in electrochemical compartments having small dimensions so as to maximize the ratio of the surface area of the reaction fluids in contact with the electrodes to the volume of reaction of fluid delimited by this surface. Such is the case in particular when the reaction involves the formation of high concentrations of unstable intermediate products and/or the use of expensive reagents. Such is also the case when it is desirable to minimize the electrical losses due to the Joule effect through the reaction fluids, or when the size constraints of the reactor are stringent in the context of the application (for example for reactors intended to be introduced into the human or animal body).

Examples of such applications which may be mentioned are the enzymatic electrochemical synthesis of diastereoisomers which require very expensive cofactors (such as NAD (nicotinamide adenine dinucleotide) or NADP (nicotinamide adenine dinucleotide phosphate) in oxidized form (NAD, $NAD^+$, NADP, $NADP^+$) or, above all, in reduced form (NADH, NADPH)) which have to be generated in situ with the aid of mediators (in particular redox mediators such FAD (flavin adenine dinucleotide) or acetyl-CoA (acylation reactions), or PAPS (3'-phosphoadenosine-5'-phosphosulfate), etc.

One of the technological solutions envisaged in this scope consists in using a reactor of the so-called microstructured type, or microreactor, and in particular with electrochemical reaction compartment(s) in the form of a channel or a plurality of parallel channels referred to as microchannel(s), of small cross section making it possible to minimize the transverse gradients of concentrations and electrical potential. The term "microchannel" refers to a channel having transverse dimensions all less than 1 mm.

U.S. Pat. No. 6,607,655 for instance describes an electrochemical reactor having electrochemical compartments with microchannels of rectangular cross section having a height less than 200 µm—preferably between 1 µm and 100 µm—and a width between 5 µm and 1 µm. In one embodiment, the microchannels are formed by grooves made on the surface of the electrodes.

Nevertheless, the teaching given by this document in this regard remains purely theoretical in so far as, on the one hand, the method for manufacturing such microstructured grooves is not given and, on the other hand, flows in microchannels with dimensions corresponding to the lower thresholds of the indicated dimensions would be accompanied, for liquids which perfectly wet the corresponding metal surface, by large pressure drops (more than $5.10^5$ Pa) which are incompatible with the use of compositions such as biological compositions liable to experience a loss of activity under excessive pressures.

Until now, only cross sections of rectangular or trapezoidal shape have been envisaged for the production of microchannels in microstructured reactors. This is because the etching and/or deposition methods which may be envisaged for producing such microchannels (for example photolithographic and screen printing methods, physical or chemical depositions, etc.) necessarily lead to such polygonal shapes with sharp corners.

However, the inventors have determined that the presence of corners, or more generally pronounced curvature variations, in the cross section of the microchannels etched in an electrode considerably impair the performances of such an electrochemical reactor, at least for the following two reasons:

it locally (in the microchannel) induces corresponding distortions of the electrical field generated by the electrode, and therefore a significant heterogeneity of the electrochemical reaction mechanism, which proves fatal in practice in view of the very small transverse dimensions and the extremely sensitive nature of the reactor (because of the great instability of the intermediate products);

in view of the wetting phenomena which assume great importance with sub-millimeter dimensions, it considerably impairs the flow of the fluid in the microchannel by tending to cause shedding of the boundary layer and inducing a very significant resistance to the flow, making it impossible in practice to use microchannels with a cross section less than 20000 $\mu m^2$ with liquids whose viscosity and surface tension are similar to those of water.

With the dimensions indicated in U.S. Pat. No. 6,607,655 and for a Peclet number less than 1000, the thickness of the diffusion layer is thus smaller than the transverse dimensions of the channel, which introduces a transverse concentration gradient that contributes to a nonuniform distribution of the electrical field. The consequence of these gradients is a low selectivity, in particular for the applications to electro-enzymatic reactions as mentioned above. For example, the concentration of the reduced form of a mediator such as flavin is not sufficient anywhere in the channel (on account of this mediator's stability) for the synthesis reaction to be spontaneous. Furthermore, a nonuniform distribution of the electrical field can induce the transformation of several chemical functions of an electro-active species, and not just specifically the target part of the molecule. Side-effects may therefore occur.

It should be noted in this regard that these problems are specific to electrochemical reactions and, in particular, are not encountered in the case of purely chemical reactions.

SUMMARY

It is an object of the invention to overcome these drawbacks by providing a method and reactor which make it possible in practice to carry out electrochemical reactions in electrochemical reaction compartments with etched microchannels, the cross section of which has an area that can be significantly less than 20000 $\mu m^2$ with improved values of yield and selectivity for the products obtained.

In order to achieve by this, the invention relates to an electrochemical reaction method in which:

a stream of a first fluid—in particular a first liquid composition or a composition containing at least one liquid phase (which may nevertheless contain a gas phase liable to be generated by the electrochemical reaction)—is passed through at least one first electrochemical reaction compartment extending between one face of a first electrode in the form of a plate and a selectively ion-permeable separating membrane, a stream of a second fluid—in particular a second liquid composition or a composition containing at least one liquid phase (which may nevertheless contain a gas phase liable to be generated by the electrochemical reaction)—is passed through at least one second electrochemical reaction compartment extending, on the opposite side from the first relative to the separating membrane, between this separating membrane and one face of a second electrode in the form of a plate, at least one electrochemical reaction compartment referred to as a microchannel compartment comprising a plurality of microchannels formed by grooves hollowed into the face of the corresponding electrode, parallel to this face, these microchannels being delimited on the opposite side from this face by the membrane pressed against this face, the corresponding fluid is circulated through the microchannels from at least one inlet for supplying fluid into the microchannel compartment to an opposite outlet for extracting fluid out of the microchannel compartment, wherein at least one microchannel compartment is used whose grooves have a cross section of at least partially curved contour with a radius of curvature greater than 30 µm and an area of between 2500 µm$^2$ and 20000 µm$^2$.

The invention also concerns an electrochemical reactor comprising:

at least one pair of electrodes in the form of plates, arranged so as to have opposing faces, a selectively ion-permeable separating membrane interposed between the electrodes of each pair of electrodes, an electrochemical reaction compartment being formed between the membrane and an opposing face of each electrode, at least one electrochemical reaction compartment referred to as a microchannel compartment comprising a plurality of microchannels formed by grooves hollowed into the face of the corresponding electrode, parallel to this face, these microchannels being delimited on the opposite side from this face by the membrane pressed against this face and extending between at least one inlet for supplying fluid into the microchannel compartment and at least one opposite outlet for extracting fluid out of the microchannel compartment, wherein the grooves have a cross section of at least partially curved contour with a radius of curvature greater than 30 µm and an area of between 2500 µm$^2$ and 20000 µm$^2$.

The said contour is at least partially curved, in the sense that it may have certain flat portions. The radius of curvature of the contour may vary along the contour. Since this radius of curvature is greater than 30 µm, the contour is free of regions where, on the one hand, the electrical field has a large orientation gradient and, on the other hand, where the flow is static in the longitudinal direction, for example because of boundary layer shedding. In particular, the contour is free of sharp corners (that is to say corners forming a concave edge). The contour is thus not polygonal. The only region of the microchannel which may have a sharp corner is the one at the junction of the contour of the groove with the membrane.

The inventors have in fact shown that such a contour, which is at least partially curved and free of sharp corners, has a specific surface substantially greater than that of a polygonal contour. Furthermore, the properties of the flow are improved.

Advantageously and according to the invention, the said contour has a curved portion extending from the said face of the electrode in contact with the membrane. Thus, in particular, the contour is free of any straight portion orthogonal to the said face of the electrode and to the said membrane. The inventors have in fact shown that such a straight portion (which would correspond to a flat side wall of the groove, orthogonal to the membrane) reduces the efficiency of the electrical field.

Preferably, advantageously and according to the invention, the said contour is entirely curved and its radius of curvature is less than 300 µm. In this embodiment, the contour is thus in particular free of straight portions (the groove is free of flat wall portions). Advantageously and according to the invention, the said contour defines an opening of the microchannel which opens onto the face of the corresponding electrode, and this contour defines a microchannel width parallel to the face of the electrode which is everywhere less than or equal to that of this opening. In this way, any point of the wall of the microchannel of one electrode faces an opposite point of the wall of a microchannel of the other electrode across the reaction compartments and the separation membrane.

More particularly, advantageously and according to the invention, the said contour is such that tangents drawn on either side of an arbitrary portion of this contour are secant outside the said contour. In other words, the said contour is free of sharp corners, which means that there is little distortion (orientation gradient) of the electrical field lines and better flow.

Advantageously and according to the invention, the said contour is a circle portion. Advantageously and according to the invention, at least one microchannel compartment is used in which the said contour is at least substantially a semicircle or a circle portion smaller than a semicircle. There is nothing to prevent the use of other similar shapes such as portions of an ellipse, parabola, hyperbola, etc. Nevertheless, a circular shape is more common, simpler and more economical to manufacture. It is furthermore the one which gives the greatest symmetry to the field lines and the reaction compartment formed in this way.

In any event, unlike a parallelepipedal geometry in particular, such a curved contour free of sharp corners makes it possible to obtain regular or even uniform distributions of the electrical potential and current by reducing the edge effects and the electrical current losses from these edges.

The inventors have demonstrated that the invention substantially makes it possible to obviate the aforementioned problems associated with the transverse gradients of concentrations and electrical field. It is thus possible to use channels whose transverse dimension can be reduced to the minimum compatible with the physical and chemical constraints, allowing the solutions to flow without affecting the activity of the products contained in the said solutions.

Advantageously and according to the invention, at least one microchannel compartment is used in which the said contour has a radius of curvature ranging from 30 µm to 300 µm—in particular of the order of 80 µm. In the case of a circle portion, the radius of curvature is constant and corresponds to that of a circle.

Likewise, reaction compartments can be obtained which have a very large specific surface that favours the production (molar flux).

Thus, advantageously and according to the invention, at least one microchannel compartment is used in which the microchannels have a specific surface, defined as the ratio of the area of the grooves to the volume inside each microchannel, of more than 250 cm$^{-1}$.

There is nothing to prevent the provision of microchannels with a variable cross section over their length for certain applications. Preferably, advantageously and according to the invention, at least one microchannel compartment is used in which each microchannel has a cross section of constant area along the microchannel. Preferably and according to the invention, the shape of the cross section remains constant over the entire length of the microchannel.

Furthermore, advantageously and according to the invention, at least one parallel-microchannel compartment is used in which the parallel grooves are mutually separated by a portion of the said face of the electrode (in contact with the membrane) in the form of a strip with a width ranging from 50 μm to 150 μm. The grooves are arranged as close as possible to one another in order to reduce the overall size of the reactor (for a constant specific surface), but their separation must also be sufficient in order to be compatible with the separating membrane, which must not intrude upon the internal volume of the microchannels (by penetration under the effect of the pressure clamping the electrodes on the membrane and/or by swelling during use).

Advantageously and according to the invention, at least one parallel-microchannel compartment is used comprising between 10 microchannels per centimeter (of width dimension) and 100 microchannels per centimeter—in particular of the order of 100 to 150 microchannels for a width of the order of 40 mm. Preferably, all the microchannels (that is to say all the grooves) are identical with respect to their shapes and dimensions.

In a method according to the invention, a first end of the microchannels is advantageously supplied with a stream of fluid, and a stream of fluid is recovered after passing through the microchannel compartment via a second end of the microchannels. In a reactor according to the invention, a first end of the microchannels thus opens into a transverse supply groove connected to a fluid inlet, and a second end of the microchannels opens into a transverse extraction groove connected to a fluid outlet. These transverse grooves preferably have a cross section which decreases from the fluid inlet and outlet, where the flow rate is greatest, so that the pressure is at least substantially constant along these transverse grooves and therefore in the various microchannels. Each transverse groove furthermore opens to the outside, for example via a slot passing through the thickness of the corresponding electrode.

The invention thus makes it possible to carry out a method of electric chemical reaction—in particular electrolytic synthesis—continuously, and the reactor according to the invention may be a continuous electrochemical reactor, each fluid inlet being supplied continuously and the reaction products being obtained with a continuous flow rate at each fluid outlet. The method according to the invention may in particular be an enzymatic electrolytic synthesis method, in particular for the preparation of diastereoisomers. In an electrolytic synthesis method according to the invention, an electrical potential difference is applied between each first electrode and each second electrode of each pair of electrodes, which are separated by an electrolytic membrane (selectively permeable to $H^+$ ions) forming an electrochemical cell. The electrodes of a reactor according to the invention are therefore connected to an electrical power supply of controlled DC voltage.

Thus, advantageously and according to the invention, at least one reaction compartment is supplied with a fluid—in particular a liquid composition or a composition containing at least one liquid phase (which may nevertheless contain a gas phase liable to be generated by the electrochemical reaction)—comprising a mediator, an enzyme and a precursor of a pyridinic cofactor selected from NADH and NADPH, the latter being regenerated continuously and quantitatively in the electrochemical reaction compartment without diluting the solution. Advantageously and according to the invention, the said fluid is a liquid composition or a composition containing at least one liquid phase (which may nevertheless contain a gas phase liable to be generated by the electrochemical reaction), and this composition is suitable for the non-racemic synthesis of diastereoisomers. In certain applications, only one of the electrochemical reaction compartments (cathodic or anodic) is a microchannel compartment according to the invention, in which case the other compartment may equally well be produced according to any other technology which is effective in practice. Nevertheless, preferably, advantageously and according to the invention, each fluid is passed through an electrochemical reaction compartment which is a microchannel compartment according to the invention.

The invention may be implemented in a reactor of small overall size. Thus, advantageously and according to the invention, electrodes in the form of plates are used, each having a thickness less than 5 mm—in particular of the order of 2 mm. It is also compatible with production in the form of a stack (or stacks) of elementary electrochemical cells (both according to the so-called monopolar type and according to the so-called bipolar type). Thus, advantageously and according to the invention, the fluids are passed in parallel through a plurality of cathodic microchannel compartments connected (in fluid communication) in parallel to the same cathodic fluid circuit, and through a plurality of anodic microchannel compartments connected (in fluid communication) in parallel to the same anodic fluid circuit, these pluralities of cathodic and anodic microchannel compartments being formed by a plurality of pairs of electrodes which are stacked and electrically connected in parallel to an electrical power supply.

The invention also concerns a method for manufacturing a reactor according to the invention.

The invention therefore relates to a method for manufacturing a microchannel electrochemical reactor, in which grooves are hollowed into at least one face of at least one electrode, wherein the grooves are etched by electroerosion using a tool which has a plurality of erosion ribs, the cross section of each erosion rib having an at least partially curved contour with a radius of curvature greater than 30 μm and an area of between 2500 $\mu m^2$ and 20000 $\mu m^2$.

Throughout the text, the term electroerosion refers to any method of shaping by the application of electrical discharges between a tool (having erosion ribs) and the article to be shaped.

Advantageously and according to the invention, the said contour of the cross section of each erosion rib is entirely curved with a radius of curvature less than 300 μm. Advantageously and according to the invention, the said contour of the cross section of each erosion rib is such that tangents drawn on either side of an arbitrary portion of this contour are secant outside the said contour.

Advantageously and according to the invention, the said contour of the cross section of each erosion rib comprises at least one circle portion—in particular at least substantially a semicircle or a circle portion smaller than a semicircle—.

Furthermore, advantageously and according to the invention, the said contour of the cross section of each erosion rib has a radius of curvature ranging from 30 μm to 300 μm—in particular of the order of 80 μm. Advantageously and according to the invention, each erosion rib has a cross section of constant area along this erosion rib. It is thus possible to use erosion ribs with a constant semicircular cross section.

Moreover, advantageously and according to the invention, erosion ribs are used which are mutually parallel in the same plane, and mutually separated in pairs by a space with a width of between 50 μm and 150 μm. Advantageously and according to the invention, a tool is used comprising a density and number of ribs adapted according to the density and number of grooves to be etched on the surface, and the tool comprises for example between 10 and 100 ribs per centimeter of width.

The invention concerns an electrochemical reaction method, an electrochemical reactor and a method for manufacturing such an electrochemical reactor, which are characterized by some or all of the characteristics mentioned above or below.

BRIEF DESCRIPTION OF THE DRAWINGS

Other objects, characteristics and advantages of the invention will become apparent on reading the following description which refers to the appended figures, in which:

FIG. 5 is a diagram illustrating a view of the face of an electrode provided with grooves forming microchannels in another alternative embodiment of an electrochemical reactor according to the invention, FIG. 8 is a schematic view in exploded perspective of an electrochemical reactor according to another alternative embodiment of the invention, comprising a plurality of stacked electrochemical cells.

DETAILED DESCRIPTION

Figure 1:
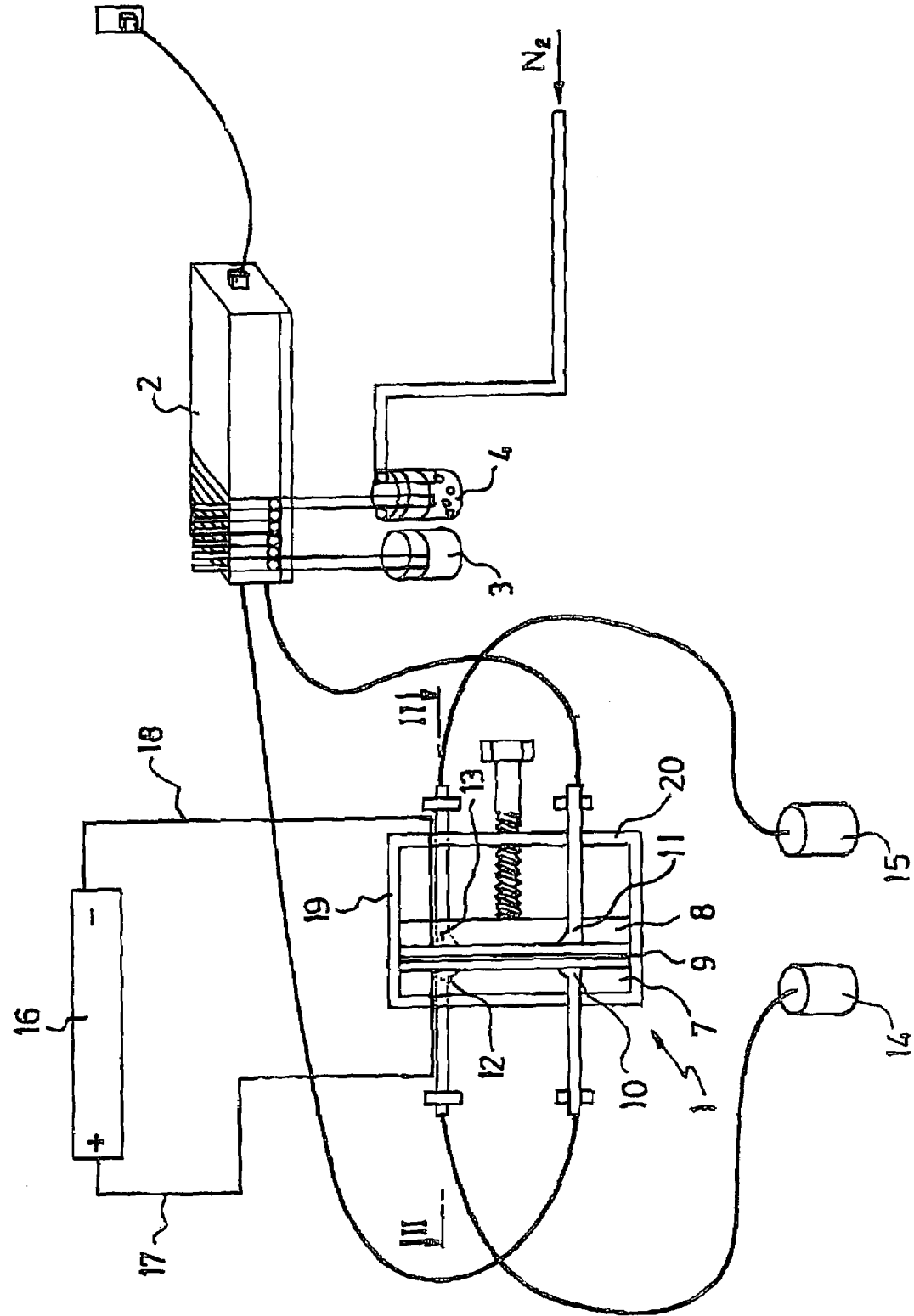
FIG. 1 is a diagram illustrating a first variant of an electrochemical reactor according to the invention, during operation for carrying out an electrochemical reaction method according to the invention.

FIG. 1 represents an illustration of the implementation of an electrochemical reaction method according to the invention, comprising a microchannel electrochemical reactor 1 according to the invention which, in the example represented, comprises a single electrochemical cell (two electrodes, namely a cathode 8 and an anode 7 which are separated by a membrane 9 as described in more detail below), an electrical peristaltic pump 2 is on the mains supply and linked to two tanks 3, 4, one 3 of which contains a liquid composition of starting electrochemical reagents for the anodic electrochemical reaction, whereas the other 4 contains a liquid composition of starting reagents for the cathodic electrochemical reaction. In the example represented, the cathodic tank 4 is connected to a source of nitrogen supplied above the liquid composition and bubbling into this liquid composition, so as to keep it under an inert atmosphere and avoid any contact with the atmospheric air in view of the instability of the cathodic reagents. Such is the case, in particular, when the cathodic reaction makes it possible to carry out enzymatic electrochemical synthesis of diastereoisomers employing unstable mediators and/or cofactors such as derivatives of nicotinamide adenine dinucleotide or flavin adenine dinucleotide.

The pump 2 makes it possible to supply on the one hand an anodic reaction compartment 5 from the tank 3 and, on the other hand, a cathodic reaction compartment 6 from the tank 4. These electrochemical reaction compartments 5, 6 are formed between each electrode 7 (anode), 8 (cathode) and the membrane 9 which separates them. The liquid composition circulates in the reaction compartment under the effect of the pressure induced by the pump 2 after having entered through a lower inlet 10 (inlet into the anodic compartment 5), 11 (inlet into the cathodic compartment 6), upwards before emerging through an upper outlet 12 (outlet of the anodic compartment 5), 13 (outlet of the cathodic compartment 6). Indeed, the reaction compartments 5, 6 preferably extend vertically and the circulation of the reaction compositions preferably takes place vertically upwards, against gravity. Each outlet 12, 13 is connected via a conduit outside the reactor 1 to a tank 14 or 15, respectively, making it possible to recover the products of the anodic or cathodic reaction, respectively.

The anode 7 is connected to the positive terminal of a DC electrical power supply 16 by a sheathed conductor wire 17. The cathode 8 is connected to the negative terminal of this electrical power supply 16 by a sheathed conductor wire 18.

Figure 2:
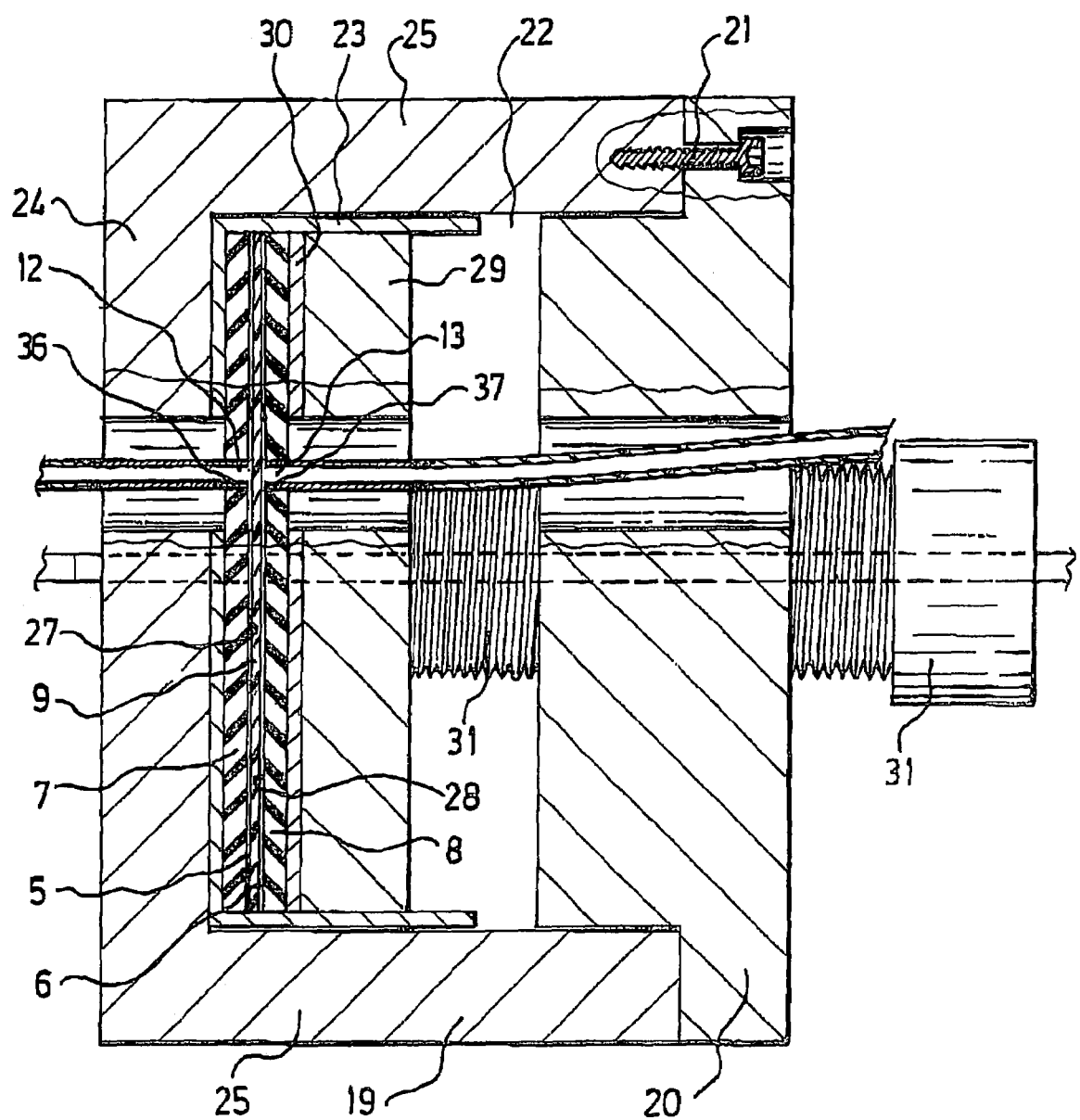
FIG. 2 is a schematic sectional view of an electrochemical reactor according to the invention, along the line II-II in FIG. 1.

The reactor 1 according to the invention is represented in more detail by FIG. 2. It comprises a rigid main outer casing 19, for example made of stainless steel or another material, depending on the application, closed by a lid 20 using screws 21. This casing 19 and this lid 20 delimit an enclosure 22 in which the electrodes 7, 8 and the membrane 9 are arranged. This enclosure 22 firstly comprises a cover lining 23 of damping, electrically insulating and antifriction synthetic material, for example PTFE, covering the bottom and the inner side walls of the casing 19. The anode 7 is a plate of electrically conductive material with a square or rectangular shape corresponding that of the lining 23 and the enclosure 22, which are arranged in the casing 19. The casing 19 has a parallelepipedal overall shape, and comprises a bottom 24 and side walls 25. It should nevertheless be noted that, during operation, the bottom 24 as well as the electrodes 7, 8 are preferably arranged vertically as represented by FIGS. 1 and 2.

The cathode 8 is also a plate of electrically conductive material, with the same format as the anode 7. The two electrodes 7, 8 are placed facing each other, with a separation membrane 9 interposed between them, that is to say between the two opposing faces 27 and 28, respectively, of the electrodes 7 and 8, respectively. The membrane 9 may, for example, be formed by a PFSA membrane (copolymer of perfluorosulfonic acid and PTFE in its acidic form ($H^+$)) as sold under the registered trademark Nafion® by DuPont Fluoroproducts, Fayetteville, USA.

The constituent materials of the two electrodes 7, 8 are selected as a function of the electrochemical reaction to be carried out in each compartment 5, 6 formed facing the membrane 9 in each of these electrodes 7, 8. In particular, the electrically conductive material may be selected from among platinum, gold, vitreous carbon, diamond, silver, copper or another metal, gold-plated copper, platinum-plated titanium or optionally insulating synthetic materials metallised by gold, etc.

The cathode 8 is pressed against the membrane 9 and the anode 7 by a piston 29, which slides in the cover lining 23 and is applied against the cathode 8 by means of a plate 30 of damping and antifriction synthetic material, for example PTFE. The piston 29 is applied against the cathode 8 by a pressure screw 31, which is engaged in a corresponding screw thread passing through the lid 20 and can be actuated from the outside in order to compress the entire stack formed by the plate 30, the two electrodes 7, 8, the membrane 9 and the lining 23 against the bottom 24.

On the side of its face 27, 28 opposing the membrane 9, each electrode 7, 8 has a plurality of microchannels formed by grooves 32 hollowed into the face 27, 28 of the corresponding electrode 7, 8, parallel to this face. On the opposite side from the face 27, 28 of the electrode 7, 8, the microchannels are delimited by the membrane 9 pressed against this plate 27, 28.

In the embodiment represented, the microchannels (that is to say the grooves 32) are mutually parallel. It should nevertheless be noted that other microchannel configurations are possible and compatible with the invention, for example microchannels which are crossed relative to one another, particularly in order to improve the flow and increase the specific surface.

The various mutually parallel and adjacent grooves 32 form a network with an overall format which is square or rectangular or in the form of a parallelogram (FIG. 5) etched into the face 27, 28 of the electrode 7, 8. The ends of the grooves 32, and therefore of the microchannels which they form, are aligned.

Each groove 32 has a cross section whose contour is at least partially curved, and has a radius of curvature greater than 30 μm, more particularly ranging from 30 μm to 300 μm—in particular of the order of 80 μm. Each groove 32 hollowed into the corresponding electrode has an opening, which opens at the surface of this electrode. The cross section of each groove 32 is such that the width of this opening is the greatest width of the groove 32. In other words, the microchannel formed by the groove 32 has a width (taken in a direction parallel to the surface of the electrode) which is everywhere less than or equal to that of the opening. In this way, each point on the surface of the wall of a microchannel of an electrode 7, 8 faces a point which lies opposite on a microchannel of the opposite electrode 8, 7, these two points being separated only by the membrane 9 and the reaction compositions. This optimises the effectiveness of the electrical field from the point of view of the electrochemical reaction. In the example represented by FIG. 3, which does not imply limitation, the contour of the cross section of each groove 32 is overall in the shape of a semicircle, the ends of this semicircle being joined by fillets to portions 33 of the face 27, 28 of the electrode 7, 8 in the form of strips coming in contact with the membrane 9. Other shapes may be adopted, in particular circle portions smaller than a semicircle, or the variants represented in FIGS. 7a to 7d which will be described below, or alternatively other shapes.

The cross-sectional area of each groove 32, that is to say of each corresponding microchannel, lies between 2500 μm² and 20000 μm². The microchannels formed in this way have a specific surface (ratio of the area of each groove 32 to the volume inside each microchannel) of more than 250 cm⁻¹. In the examples represented, and according to the invention, each microchannel has a cross section whose area is constant along the microchannel. The same is true of the shape of the microchannel, which remains constant over its length. In other words, the microchannel has the general shape of a cylinder (in the mathematical sense of the term) The width of the strip portions 33 separating two grooves 32 is a small as possible, and advantageously lies between 50 μm and 150 μm.

FIG. 5 represents the example of a face 27 of an anode 7 in contact with the membrane 9.

The various parallel grooves 32 open at their ends into two transverse grooves, i.e. a supply groove 34 and an extraction groove 35. Each of these transverse grooves is hollowed into the face 28 of the corresponding electrode 8 with a depth at least equal to that of the grooves 32. The lower transverse groove 34 is a supply groove, which is connected in communication with the inlet 11 of the reagent composition through the thickness of the plate forming the electrode 8. The inlet 11 is formed at one of the ends of the transverse supply groove 34, where the latter has a greater width. The transverse supply groove 34 extends along the lower ends of the grooves 32 in order to supply the corresponding microchannels, and its width decreases as far as its end which lies opposite the inlet 11, as represented by FIG. 5.

As for the grooves 32 forming the microchannels, the transverse grooves 34, 35 have a cross section whose contour is at least partially curved. In particular, it is free of sharp corners. This contour is preferably a circle portion, in particular at least substantially a semicircle. Level with the inlets 10, 11 and the outlets 12, 13, the width of the transverse groove 34, 35 is at least equal to the diameter of the orifices forming these inlets 10, 11 and outlets 12, 13.

The upper transverse groove 35 is an extraction groove, which receives the liquid having circulated in the microchannels and which extends next to the upper ends of the grooves 32 in order to recover this liquid. The outlet 13 is in communication with the transverse extraction groove 35, and is arranged at an end of this transverse extraction groove 35 which is diagonally opposite that of the supply groove 34 receiving the inlet 11. The outlet 13 is made through the thickness of the plate forming the electrode 8.

As represented by FIG. 2, each inlet 10, 11 and each outlet 12, 13 is formed by a hole receiving a tube 36, 37 introduced and welded into this hole.

The width of the extraction groove 35 increases from its end lying opposite the outlet 13 as far as the end receiving this outlet 13. The width variation of the transverse grooves 34, 35 is adapted so that the speed and pressure in these grooves 34, 35 remain substantially constant, taking into account the parallel arrangement of the various microchannels to which they are connected.

It should be noted that the preferred embodiment represented by FIG. 5 does not correspond to that of FIG. 2 as regards the arrangement of the inlets 11 and outlets 13. Furthermore, the grooves 32, 34, 35 are not represented in FIG. 2.

The embodiment of FIG. 5 is advantageously suitable for producing a plurality of electrochemical cells stacked against one another. This is because the electrode plate may then have a network of grooves 32 hollowed onto each of its main faces. On the face opposite the one represented by FIG. 5, transverse grooves (similar to those 34, 35 described above and represented) communicate with the inlet 11 and with the outlet 13. One of the faces of the plate makes it possible to produce one electrochemical compartment (anodic in the example given), whereas the opposite face makes it possible to produce another electrochemical compartment. The various plates stacked via membranes 9 form a plurality of electrochemical cells, each comprising an anodic compartment and a cathodic compartment, which are connected in parallel to one of the fluid supply/extraction circuits. The anodic fluid supply/extraction circuit in the anodic compartments is separate from the cathodic fluid supply/extraction circuit in the cathodic compartments.

The exemplary embodiment represented by FIG. 8 illustrates a so-called monopolar type assembly of an electrochemical reactor according to the invention, comprising a stack of a plurality of electrochemical cells. In the example represented, the reactor comprises two anode plates 7a, 7b and two cathode plates 8a, 8b. Each of the plates is similar to the one represented by FIG. 5 and has grooves 32, 34, 35, and therefore microchannels, on each of its faces, that is to say on the front and back faces. The microchannels and grooves formed on each face are aligned facing one another, and are superposed in the transverse direction orthogonal to the thickness of the plates 7a, 7b and 8a, 8b. In other words, the grooves 32, 34, 35 formed on one face of one of the plates are symmetrical with those arranged on the other face of the same plate, with respect to a mid-plane parallel to the main faces of this plate.

Conversely, the transverse grooves 34, 35 of the anode plates 7a, 7b are offset relative to those of the cathode plates 8a, 8b, so that the microchannels of the anode plates communicate with the inlets 11 and outlets 13 arranged on a first diagonal, whereas the microchannels of the cathode plates communicate with the inlets 10 and outlets 12 arranged on another diagonal.

The body 25 of the reactor and the Teflon® lining 23 are recessed on two opposite side faces so as to have lateral slots 81 allowing the passage of lateral extensions 87 and 88, respectively, of the anode plates 7a, 7b and cathode plates 8a, 8b, respectively. Each plate preferably comprises two diagonally opposite lateral extensions 87, 88 so as to ensure balanced arrival of the current on either side of the electrode.

The Teflon® base covering the bottom 24 of the reactor, as well as this bottom 24, are pierced by two bores in the lower part, which communicate with the inlet orifices 10, 11 of the plates 7a, 7b and 8a, 8b in order to supply the microchannels.

As can be seen in FIG. 8, the format of the microchannels of the anode plates 7a, 7b is in the shape of a parallelogram offset relative to that of the microchannels of the cathode plates 8a, 8b, so that one 90 of the fluid inlet bores faces one of the orifices of these plates 7a, 7b constituting the inlet 10 of fluid into the anodic compartments, whereas the other inlet bore 91 is in fluid communication with the inlet orifices 11 of the cathodic compartments.

The microchannels of the anode plates 7a, 7b correspond only with the inlet orifices 10, and the microchannels of the cathode plates 8a, 8b correspond only with the inlet orifices 11. The bores 90, 91 are connected to fluid supply tubes 92, 93.

In the example represented, the Teflon® base is surmounted by a first membrane 9a, itself covered by an anode plate 7a covered by a second membrane 9b covered by a first cathode plate 8a, covered by a third membrane 9c, covered by a second anode plate 7b, covered by a fourth membrane 9d, covered by a second cathode plate 8b, covered by a fifth membrane 9e, itself covered by a Teflon® plate 30, then by a piston 29, the assembly being compressed in the thickness direction by the clamping screw 31 carried by the lid 20 screwed onto the body 25, as in the embodiment of FIG. 2.

The upper outlet orifices, i.e. 12 of the anodic compartments and 13 of the cathodic compartments, respectively connected to the microchannels of the various anodic plates 7a, 7b and cathodic plates 8a, 8b, respectively, are in fluid communication with one another and with fluid outlet tubes 94 and 95, respectively, one 94 for extracting the reaction fluid out of the anodic compartments and the other 95 for extracting the reaction fluid out of the cathodic compartments.

The outlet tubes 94, 95 pass through bores made in the lid 20 and in the piston 29, in order to be associated with the orifices made through the Teflon® plate 30 which receives the fluids from the electrochemical compartments.

The membranes 9a, 9b, 9c, 9d are all also pierced by through-orifices facing the inlets 10, 11 and outlets 12, 13 of the plates 7a, 7b, 8a, 8b in order to allow circulation of the fluid through the various plates and the various membranes, from the inlet tubes 92, 93 into the outlet tubes 94, 95. As indicated above, however, the anodic circuit is separate from and independent of the cathodic circuit.

The electrical connection extensions 88 of the cathode plates 8a, 8b are offset laterally relative to those 87 of the anode plates 7a, 7b so as to avoid any risk of short-circuit.

As can be seen, such an assembly is extremely simple, economical and makes it possible to stack a large number of electrochemical cells. All the anodic electrical connection extensions 87 are connected to the electrical supply wire of the positive terminal of the electrical power supply 16, and all the cathodic electrical connection extensions 88 are connected to the supply wire 18 connected to the negative terminal of the electrical voltage source 16.

Figure 6A:
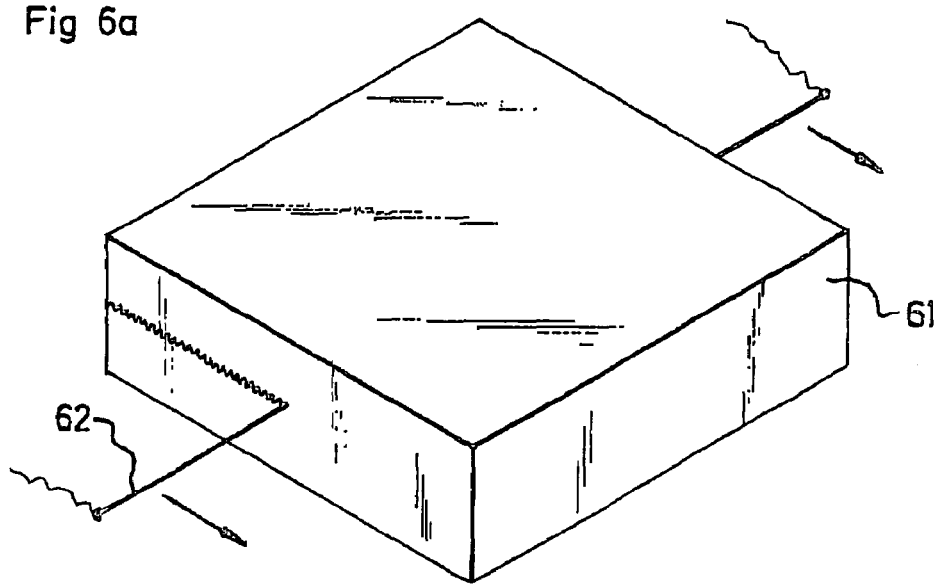
FIGS. 6a to 6c are diagrams illustrating three steps of a manufacturing method according to the invention.
Figure 6B:
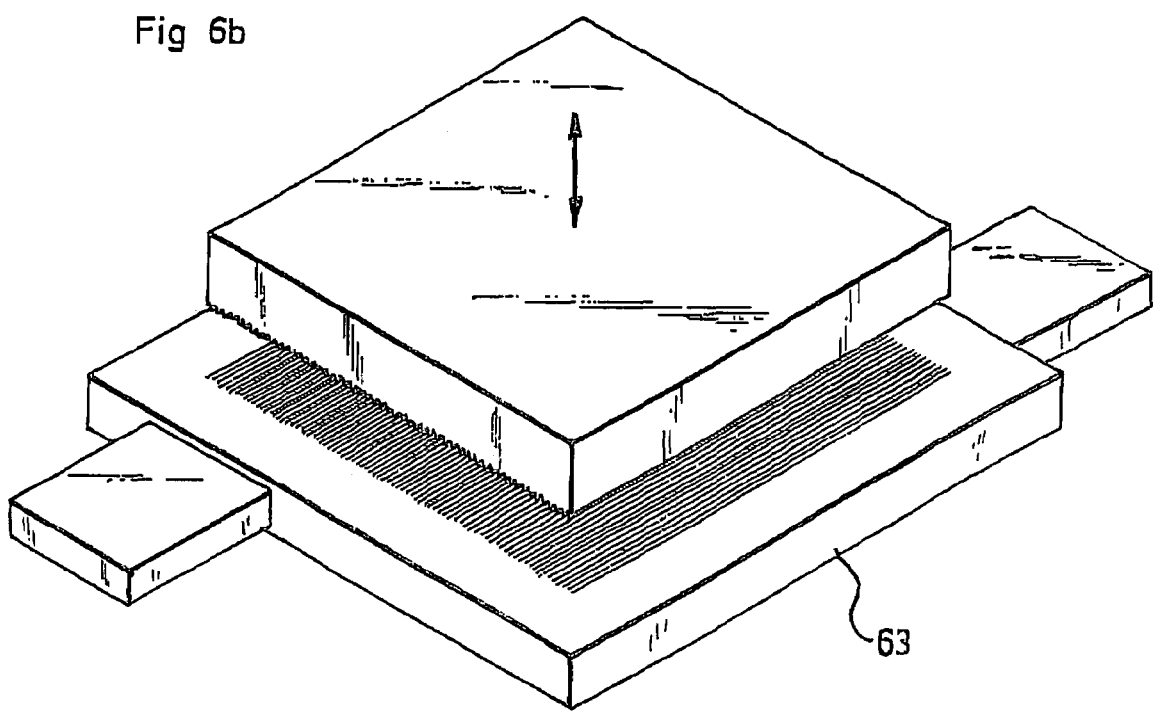
Figure 6C:
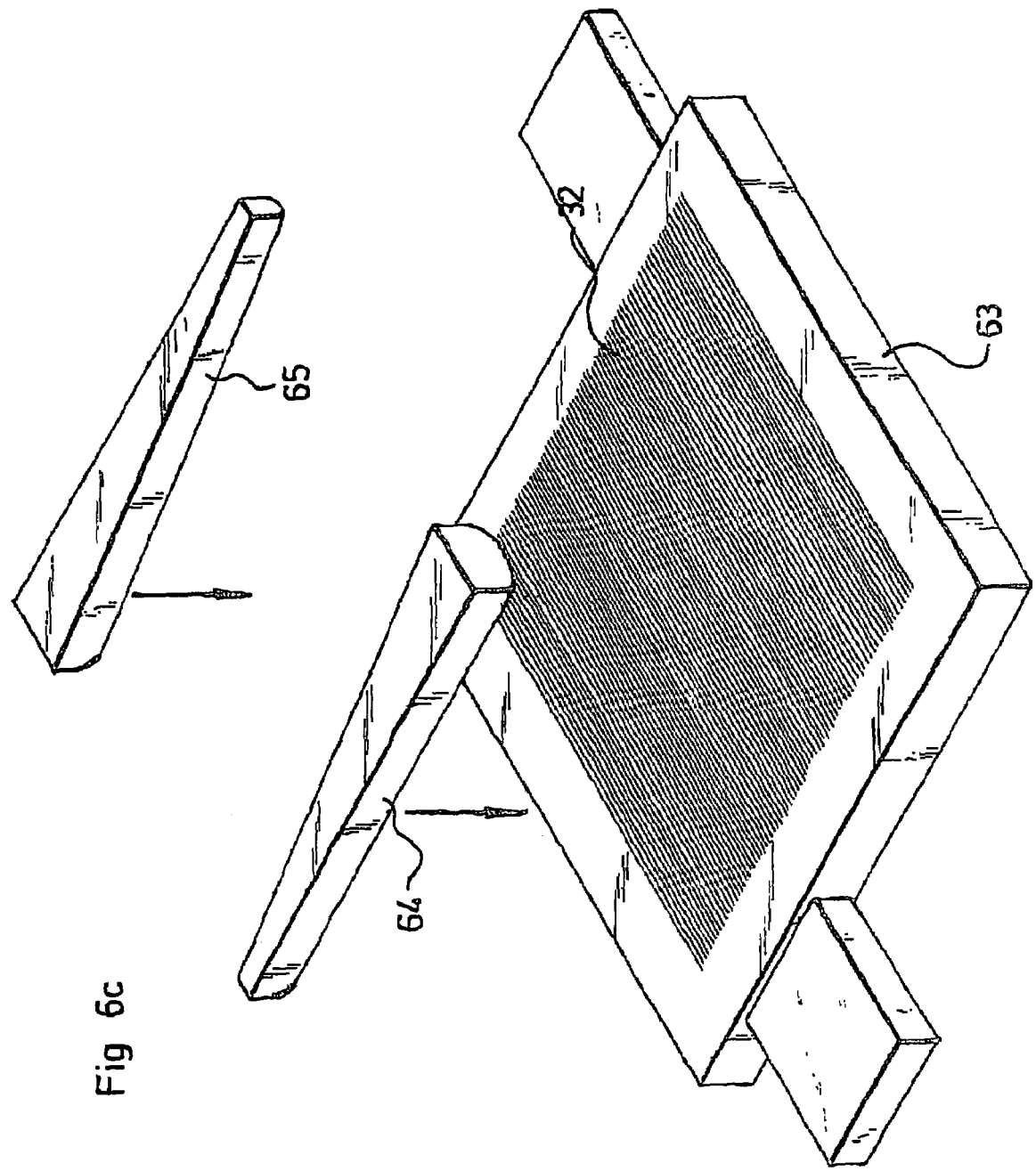

FIGS. 6a to 6c illustrate various steps of a method for manufacturing a face of an electrode of an electrochemical reactor according to the invention. The first step represented by FIG. 6a starts with a block 61 of electrically conductive material, for example copper, which is cut using an electroerosion wire 62 that is moved in this block 61. An electroerosion installation and method well known per se are used in order to perform this cutting.

The entire cutting process is generally carried out in a bath of liquid with low electrical conductivity, aiding the formation of sparks, cooling the article and evacuating the vapours and molten cuttings. The electroerosion wire 62 is connected to a suitable electrical power supply and may be guided by an automatic robot. The movement of the electroerosion wire 62 is adapted in order to form a negative impression in the copper block 61, which impression corresponds to the negative image of the shape of the grooves 32 to be etched in the electrode plate.

In the step of FIG. 6b, the block 61 is moved next to a plate 63 of a conductive material corresponding to the constituent material of the electrode to be etched. The impression of the block 61 is oriented towards the face of the plate in which the grooves 32 are to be etched. The block 61 is used as an electroerosion tool in order to etch this plate 63 so as to form the grooves 32 in it, as described above.

FIG. 6c represents the production of the transverse grooves 34, 35 with the aid of blocks 64, 65, which are used as electroerosion tools in order to produce these transverse grooves 34, 35.

The holes corresponding to the inlets 10, 11 and the outlets 12, 13 are likewise produced by electroerosion.

Using an electroerosion technique in order to produce the grooves 32 allows these grooves 32 to be given almost any profile with extreme precision and very small dimensions.

Figure 4:
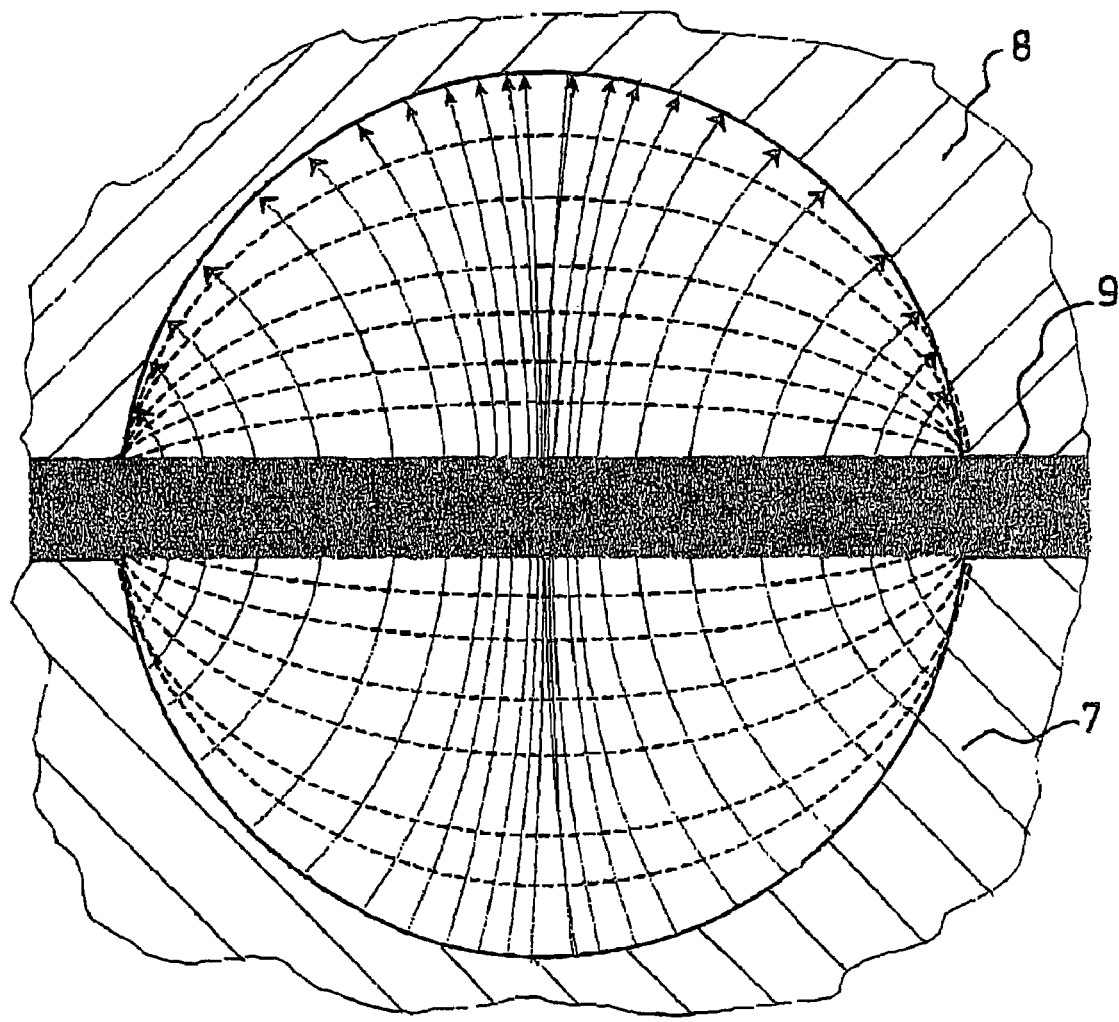
FIG. 4 is a diagram illustrating the distributions of the field lines in two microchannels which are separated by a membrane in an electrochemical reactor according to the invention.

FIG. 4 represents the electrical field lines obtained on either side of a membrane 9 within two opposing microchannels, one formed in the anode 7 and the other in the cathode 8, assuming that the cross section of the microchannels corresponds exactly to a half-disc. As can be seen, the field lines are distributed very uniformly within each microchannel with relatively little distortion. In this way, the liquid composition inside each microchannel experiences the influence of the electrical field homogeneously throughout the cross section of the microchannel. It should be noted that FIG. 4 is a theoretical representation since, as indicated above, in practice the contour of the cross section of the grooves 32 does not join with the strip portions 33 in contact with the membrane 9 by sharp edges as represented in FIG. 4, but by fillets.

FIGS. 7a to 7d represent some other variants which may be envisaged for production of the grooves 32 forming the microchannels.

Figure 7A:
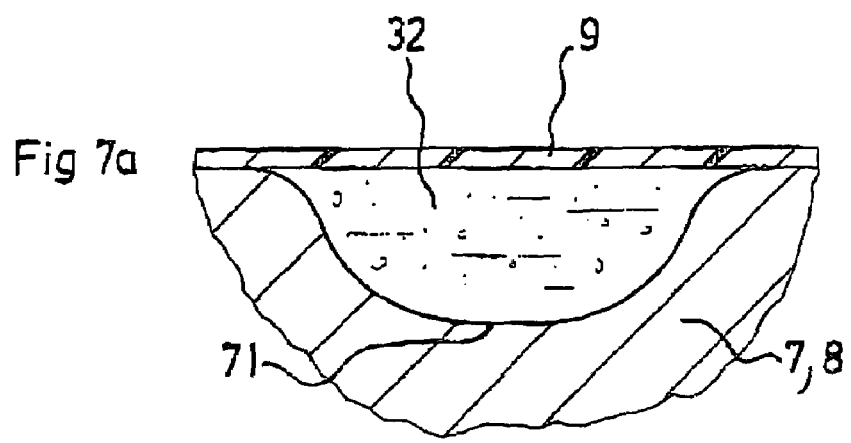
FIGS. 7a to 7d are cross-sectional diagrams illustrating various examples of possible variants of contour shapes of the grooves which may be used to form microchannels in an electrochemical reactor according to the invention.

In FIG. 7a, the groove 32 has been widened by inserting a flat portion 71 into its most concave base part parallel to the membrane 9. This flat portion 71 is interposed between two circular portions joining the bottom 71 of the groove 32 to the portion 33 of the face of the electrode 7, 8 in contact with the membrane 9.

Figure 7B:
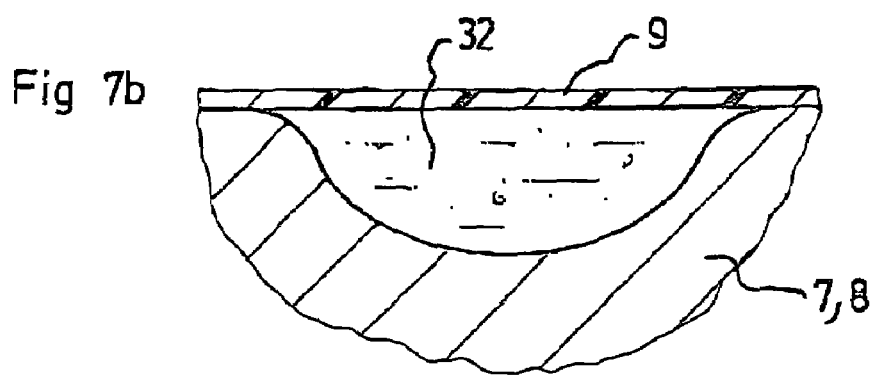

In FIG. 7b, the contour of the cross section of the groove 32 has the general shape of a semi-ellipse cut along its major axis, that is to say it is wider than a semicircular groove.

Figure 7C:
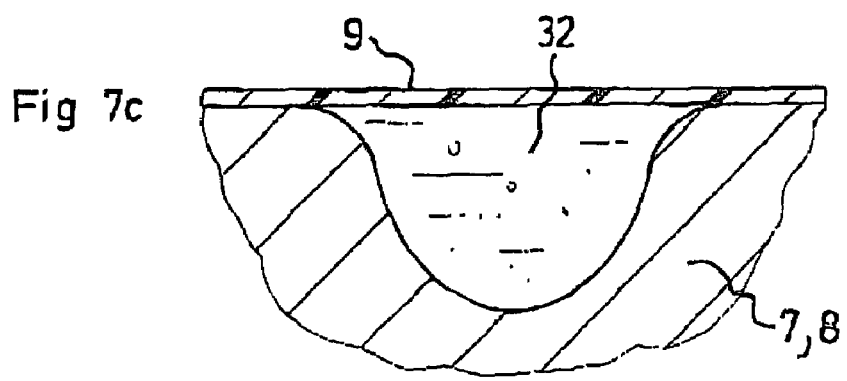

In FIG. 7c, the contour of the cross section of the groove 32 has the general shape of a parabola portion.

Figure 7D:
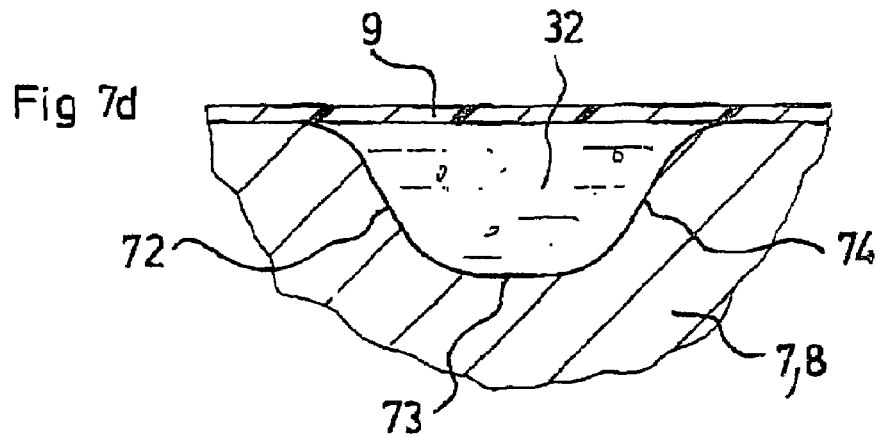

In the variant of FIG. 7d, the contour of the cross section of the groove 32 has three flat portions 72, 73, 74 joined by curved portions.

The contour of the cross section of the grooves 32 and of the microchannels is concave overall, apart from the connecting fillets forming convex portions.

Other alternative embodiments may be envisaged so long as the contour is free of sharp corners, that is to say free of abrupt variations in radius of curvature.

A very large number of microchannels, each forming an electrochemical reaction compartment, may be provided in a reactor according to the invention. In particular, between 10 microchannels per centimeter of width and 100 microchannels per centimeter of width may be provided, forming a network whose width is also several centimeters, each microchannel having a transverse dimension which may lie between 30 μm and 300 μm.

As represented by FIG. 1, electrolytic synthesis or another electrochemical reaction may thus be carried out continuously.

The dimensions of the microchannels make it possible in practice to create electrolytic compartments which individually have a very small volume relative to their electrolyte/electrode contact surface (that is to say a very large specific surface); furthermore, the facts that the electrical field is homogeneous inside each microchannel and that the flow is not impeded by the presence of sharp corners lead to conditions conducive to directing the chemical reactions associated with the electrochemical reaction, in particular by some reactions which are unfavourable on the macroscopic scale being made spontaneous. Furthermore, the reactions which take place in each microchannel have a very high conversion ratio, close to total transformation after a single pass through the reactor in the case of fast electrochemical systems such as the potassium ferri/ferrocyanide redox pair. Moreover, the low overall internal resistance (typically of the order of 0.05 Ω) allows the electrical power loss during the electrolysis to be reduced considerably. The high specific surface, more than 250 $cm^{-1}$, makes it possible to obtain a relatively high productivity, typically of the order of 4.5 mol/h/$m^2$.

The invention is thus applicable to the conduct of optionally catalysed electrochemical syntheses in chemistry and biochemistry, optionally assisted by enzymes. In particular, it is applicable to the conduct of electrolytic syntheses in which indirect regeneration of cofactors such as NADH and NADPH is carried out, for example by using the mediator FAD. It is therefore possible to carry out the electrolytic synthesis, for example of diastereoisomers, enzymatically in a single pass, that is to say in a single step, in a reactor according to the invention.

EXAMPLE

Figure 3:
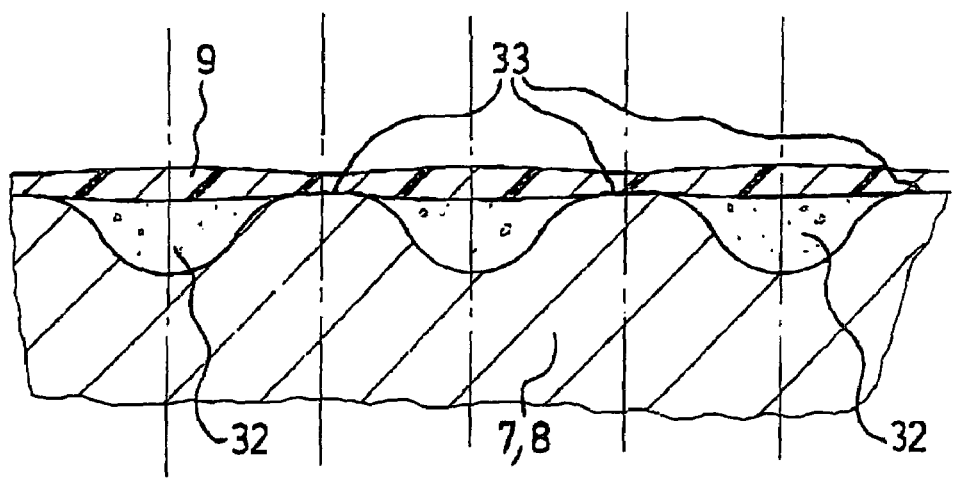
FIG. 3 is a schematic detailed view in enlarged cross section of a part of a microchannel compartment, illustrating an example of a contour shape of the grooves forming microchannels of an electrochemical reactor according to the invention.

A reactor as represented in FIGS. 1 and 2 is used, having a cathodic membrane 9 reference N1135/3.5 MIL 1100EW with a gold cathode 8 and a platinum anode 7. Each electrode is provided with one hundred and thirty-three semicircular grooves 32 as represented in FIG. 3, having a radius of curvature of the order of 80 μm. Each electrode 7, 8 has dimensions of 50 mm×50 mm×2 mm.

The length of each microchannel is 32 mm.

Figure 9:
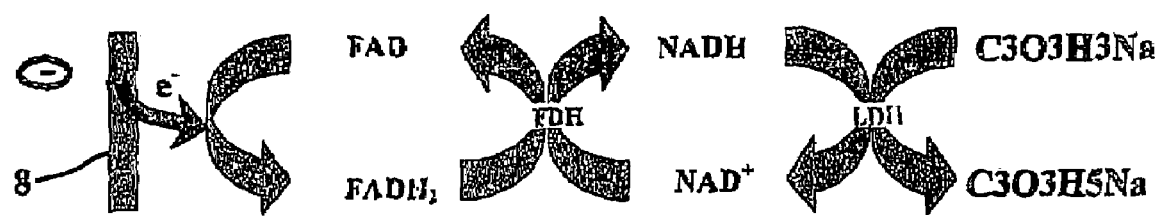
FIG. 9 is a diagram of an example of an electrochemical reaction which may be carried out using the invention.

This reactor is used to carry out the electrolytic synthesis of l-lactate ($C_3O_3H_5Na$) from pyruvate ($C_3O_3H_3Na$) used as an example of an enzymatic substrate. The regeneration of the NADH takes place by indirect electrochemical means, with mediation by a flavin. The reaction scheme represented in FIG. 9 illustrates the overall process.

The starting cathodic liquid composition (tank 4) therefore comprised the mediator FAD, the cofactor $NAD^+$ in oxidized form, the enzyme formate dehydrogenase FDH, l-lactate dehydrogenase l-LDH and sodium pyruvate ($C_3O_3H_3Na$) in phosphate buffer at pH=7.0.

Table 1 below gives the precise references of the starting compounds used. The analyses were carried out by HPLC chromatography using sodium acetate as an internal standard.

FAD: ACROS-84366-81-A
FDH: SIGMA-ALDRICH-CE1.21.2 yeast batch 0122K0363
β-$NAD^+$: ACROS-53 84-9
β-NADH: SIGMA-ALDRICH-EC 210-123-3
l-LDH of rabbit muscle: SIGMA-ALDRICH-EC No 2326178
Sodium pyruvate, 99%: ACROS-112-24-6

The operating conditions were as follows: temperature: 20° C.; phosphate buffer at 0.05 M; pH=7.0; nitrogen pressure: $10^5$ Pa.

Table 2 below gives the results obtained in nine different tests.

| | Test No | | | | | | | | |
|---|---|---|---|---|---|---|---|---|---|
| | 1 | 2 | 3 | 4 | 5 | 6 | 7 | 8 | 9 |
| [β-$NAD^+$]° mM | 4.21 | 4.50 | 3.91 | 3.88 | 3.84 | 3.84 | 3.84 | 4.04 | 4.04 |
| [FAD]° mM | 4.24 | 4.90 | 3.94 | 3.91 | 4.11 | 4.11 | 4.11 | 4.81 | 4.81 |
| [FDH]° g/l | 1 | 1 | 0.5 | 0.5 | 0.8 | 0.5 | 0.5 | 0.5 | 0.5 |
| [l-LDH]° units/$cm^3$ | 0.025 | 5 | 2 | 2 | 5.1 | 5 | 5 | 5 | 0.5 |
| [sodium pyruvate] mM | 1.92 | 3.72 | 2.89 | 2.81 | 2.86 | 2.87 | 2.87 | 1.38 | 1.38 |
| number of passes through the reactor | | | | 1 | | Continuous recycling | Discontinuous recycling 2 times | | Discontinuous recycling 3 times |

-continued

| | Test No | | | | | | | | |
|---|---|---|---|---|---|---|---|---|---|
| | 1 | 2 | 3 | 4 | 5 | 6 | 7 | 8 | 9 |
| $\Phi_{anolyte} = \Phi_{catholyte}$ (cm$^3$/h) | 7.5 | 7.5 | 7.5 | 1.8 | 5.6 | 0.5 | 1.8 | 3.8 | 3.8 |
| residence time (s) | 27 | 27 | 27 | 108 | 37 | 423 | 108 | 109 | 109 |
| applied potential (mV) | −500 | −600 | −600 | (−6.5 mA) | −600 | −300 | −600 | −600 | −600 |
| % conversion (pyruvate relative to l-lactate) | 17.3 | 22.2 | 22.9 | 19.6 | 38.5 | 40.6 | 35.5 | ~99 | ~99 |
| TN (h$^{-1}$) | 10.35 | 24.10 | 22.25 | 4.66 | | 2.58 | | 9.43 | 9.43 |
| production of l-lactate (mol/m$^2$/day) | 0.038 | 0.094 | 0.075 | 0.016 | 0.092 | 0.008+ | 0.029 | 0.078 | 0.078 |

TN is the ratio of the number of moles of l-lactate to the initial number of moles of β-NAD$^+$ divided by the residence time in the microreactor. In other words, it is the number of regeneration cycles of the coenzyme β-NAD$^+$.

The electrochemical synthesis is carried out in the cathodic compartment 6. In test No 5, the composition is recycled continuously in the reactor with a recycling factor of 0.25. In test No 7, the composition is recycled discontinuously once in the reactor (two passes in total). In tests 8 and 9, the sample is recycled discontinuously twice in the microreactor (three passes in total). No known device of the prior art makes it possible to obtain such results.

On the side of the anodic compartment 5, the starting composition is 0.05 M phosphate buffer at pH 7.0 and the reaction which takes place is the oxidation of water:
$2H_2O \rightarrow O_2 + 4H^+ + 4e^-$ In tests No 8 and 9, as can be seen, an almost complete pyruvate to l-lactate conversion ratio is obtained in three passes through the reactor; this indicates that the yield of the electrochemical reaction is quantitative, that the yield of the first chemical reaction (FADH$_2$/NAD$^+$/FDH) is quantitative and that the yield of the second chemical reaction (NADH/pyruvate/l-LDH) is also quantitative. In fact, the product of three values is equal to 1 only if the three values are themselves equal to 1. Such a result had never been obtained before on the prior art.

The invention is thus advantageously applicable to selective methods for quantitatively regenerating pyridinic cofactors of the NADH and NADPH type. It applies in particular to the non-racemic synthesis of diastereoisomers, in particular l-lactate with quantitative chemical yields, by continuously and quantitatively regenerating the pyridinic cofactors of the NADH and NADPH type, without diluting the solution.

The invention may of course be subject to very many variants and applications other than those mentioned above. In particular, a reactor according to the invention may be used for other types of electrochemical reactions in which the same technical problems arise.

The invention claimed is:

1. An electrochemical reaction method, comprising:
   passing a stream of a first fluid through at least one first electrochemical reaction compartment extending between a reaction face of a first electrode and a first side of a selectively ion-permeable separating membrane pressed against said reaction face;
   passing a stream of a second fluid through at least one second electrochemical reaction compartment extending between a reaction face of a second electrode and a second side of said selectively ion-permeable separating membrane pressed against said reaction face, said second side being opposite from said first side, wherein
   at least one of said first electrochemical reaction compartment and said second electrochemical reaction compartment is supplied with said stream of a first fluid or said stream of a second fluid, the stream further comprising at least one liquid phase,
   said first and second electrodes are each in the form of a plate made of an electrically conductive material selected from the group consisting of vitreous carbon, metallic materials, and metallised insulating synthetic materials metallised by gold,
   said first and second electrodes are connected to an electrical power supply creating an electrical field between said first and second electrodes, and
   at least one of said first electrochemical reaction compartment and said second electrochemical reaction compartment is a microchanneled compartment comprising a plurality of microchannels formed by grooves hollowed into said reaction face of said at least one of said first electrochemical reaction compartment and said second electrochemical reaction compartment, said grooves extending parallel to said reaction face, each microchannel being formed and delimited by a groove and by said selectively ion-permeable separating membrane pressed against said reaction face and said groove; and
   circulating said stream through said microchannels, from at least one inlet of said microchanneled compartment for supplying the first fluid or the second fluid into said at least one of said first electrochemical reaction compartment and said second electrochemical reaction compartment, to an opposite outlet of said microchanneled compartment for extracting the first fluid or the second fluid out of said at least one of said first electrochemical reaction compartment and said second electrochemical reaction compartment,
   wherein at least one said microchanneled compartment is used whose grooves have a cross section of at least partially curved contour with a radius of curvature greater than 30 µm and an area of between 2500 µm$^2$ and 20000 µm$^2$.

2. The method as claimed in claim 1, wherein at least one said microchanneled compartment is used in which said contour has a curved portion extending from said reaction face.

3. The method as claimed in claim 1, wherein at least one said microchanneled compartment is used in which said contour is entirely curved, and has a radius of curvature less than 300 μm.

4. The method as claimed in claim 1, wherein at least one said microchanneled compartment is used in which said contour defines an opening of the groove which opens onto said reaction face, and a groove width parallel to said reaction face which is everywhere less than or equal to that of said opening.

5. The method as claimed in claim 1, wherein at least one said microchanneled compartment is used in which said contour is such that tangents drawn on either side of an arbitrary portion of said contour are secant outside said contour.

6. The method as claimed in claim 1, wherein at least one said microchanneled compartment is used in which said contour is a circle portion.

7. The method as claimed in claim 1, wherein at least one said microchanneled compartment is used in which said contour is at least substantially a semicircle.

8. The method as claimed in claim 1, wherein at least one said microchanneled compartment is used in which said contour has a radius of curvature ranging from 30 μm to 300 μm.

9. The method as claimed in claim 1, wherein at least one said microchanneled compartment is used in which said contour has a radius of curvature of the order of 80 μm.

10. The method as claimed in claim 1, wherein at least one said microchanneled compartment is used in which the microchannels have a specific surface, defined as the ratio of the area of the grooves to the volume inside each microchannel, of more than $250\ cm^{-1}$.

11. The method as claimed in claim 1, wherein at least one said microchanneled compartment is used in which each microchannel has a cross section of constant area along the microchannel.

12. The method as claimed in claim 1, wherein at least one said microchanneled compartment is used in which the grooves are parallel to each other and to said reaction face, and mutually separated by a portion of said reaction face in the form of a strip with a width ranging from 50 μm to 150 μm.

13. The method as claimed in claim 1, wherein in at least one said microchanneled compartment, a first end of the microchannels is supplied with the stream of first fluid or the stream of second fluid, and the stream of first fluid or the stream of second fluid is recovered after passing through the microchannels via a second end of the microchannels.

14. The method as claimed in claim 1, wherein at least one said microchanneled compartment is used comprising between 10 microchannels per centimeter and 100 microchannels per centimeter.

15. The method as claimed in claim 1, wherein said first and second electrodes in the form of plates are used, each having a thickness less than 5 mm.

16. The method as claimed in claim 1, wherein the fluids are passed in parallel through a first plurality of said microchanneled compartments connected in parallel to a same cathodic fluid circuit, and through a second plurality of said microchanneled compartments connected in parallel to a same anodic fluid circuit, each of said first and second pluralities of microchanneled compartments being formed by a plurality of pairs of said first and second electrodes, which are stacked with interposed selectively ion-permeable separating membranes, and electrically connected in parallel to the electrical power supply.

17. The method as claimed in claim 1, wherein at least one of said first fluid and said second fluid as supplied to said microchanneled compartment is a composition containing the at least one liquid phase.

18. The method as claimed in claim 1, wherein at least one of said first electrochemical reaction compartment and said second electrochemical reaction compartment is supplied with said first fluid or said second fluid comprising a solution of a mediator and a precursor of a pyridinic cofactor selected from NADH and NADPH, and the precursor is regenerated continuously and quantitatively in the electrochemical reaction compartment without diluting the solution.

19. The method as claimed in claim 18, wherein at least one of said first fluid and said second fluid is a liquid composition suitable for the non-racemic synthesis of diastereoisomers.

20. The method as claimed in claim 1, wherein said first electrochemical reaction compartment is electrically connected to a positive terminal of the electrical power supply, and said second electrochemical reaction compartment is electrically connected to a negative terminal of the electrical power supply.

21. The method as claimed in claim 1, wherein each of said first electrochemical reaction compartment and said second electrochemical reaction compartment is a microchanneled compartment.

22. The method as claimed in claim 1, wherein in each microchanneled compartment, said first fluid and said second fluid is a composition containing at least one liquid phase and is pumped under pressure so as to circulate in said microchanneled compartment from said inlet to said outlet.

* * * * *

UNITED STATES PATENT AND TRADEMARK OFFICE
CERTIFICATE OF CORRECTION

PATENT NO. : 7,662,270 B2
APPLICATION NO. : 11/281434
DATED : February 16, 2010
INVENTOR(S) : Tzedakis et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1092 days.

Signed and Sealed this

Twenty-eighth Day of December, 2010

David J. Kappos
*Director of the United States Patent and Trademark Office*